(12) United States Patent
van Dam et al.

(10) Patent No.: US 7,996,070 B2
(45) Date of Patent: Aug. 9, 2011

(54) TEMPLATE MATCHING METHOD FOR MONITORING OF ECG MORPHOLOGY CHANGES

(75) Inventors: Peter van Dam, Doesburg (NL); Suzanne Mouton, Ravenstein (NL); Peter Oosterhoff, Zutphen (NL)

(73) Assignee: Medtronic, Inc., Minneapolis, MN (US)

( * ) Notice: Subject to any disclaimer, the term of this patent is extended or adjusted under 35 U.S.C. 154(b) by 659 days.

(21) Appl. No.: 12/108,655

(22) Filed: Apr. 24, 2008

(65) Prior Publication Data
US 2009/0270747 A1   Oct. 29, 2009

(51) Int. Cl.
*A61B 5/0472* (2006.01)

(52) U.S. Cl. ............. 600/509; 600/483; 600/513; 607/6

(58) Field of Classification Search .................. None
See application file for complete search history.

(56) References Cited

U.S. PATENT DOCUMENTS

| | | | |
|---|---|---|---|
| 5,313,953 A | 5/1994 | Yomtov et al. | |
| 5,593,431 A | 1/1997 | Sheldon | |
| 5,865,760 A | 2/1999 | Lidman et al. | |
| 6,044,297 A | 3/2000 | Sheldon et al. | |
| 6,393,316 B1 | 5/2002 | Gillberg et al. | |
| 6,975,904 B1 | 12/2005 | Sloman | |
| 7,039,463 B2 | 5/2006 | Marcovecchio | |
| 7,062,315 B2 | 6/2006 | Koyrakh et al. | |
| 7,103,405 B2 | 9/2006 | Sarkar et al. | |
| 7,130,677 B2 | 10/2006 | Brown et al. | |
| 7,336,999 B1 | 2/2008 | Koh | |
| 2002/0091331 A1* | 7/2002 | Onoda et al. | 600/509 |
| 2004/0093035 A1 | 5/2004 | Schwartz et al. | |
| 2006/0111643 A1 | 5/2006 | Cazares et al. | |
| 2007/0149890 A1 | 6/2007 | Li et al. | |
| 2007/0156057 A1 | 7/2007 | Cho et al. | |
| 2008/0177194 A1* | 7/2008 | Zhang et al. | 600/513 |
| 2009/0048528 A1 | 2/2009 | Hopenfeld et al. | |

FOREIGN PATENT DOCUMENTS
WO   2008153450   12/2008

OTHER PUBLICATIONS

Wolber et al., "Wavelet-Based Tachycardia Discrimination in ICDS: Impact of Posture and Electrogram Configuration", Cardiovascular Center, Cardiology, University Hospital Zurich, Zurich, Switzerland, PACE, vol. 29, pp. 1255-1260.
International Search Report, PCT/US2009/041204, 4 pages.

* cited by examiner

*Primary Examiner* — Kennedy J Schaetzle
(74) *Attorney, Agent, or Firm* — Stephen W. Bauer; Reed A. Duthler

(57) ABSTRACT

An implantable medical device and associated method perform ECG morphology monitoring. A subcutaneous ECG signal and a posture signal are sensed in a patient. A cardiac condition is detected in response to the ECG signal and the posture signal. In one embodiment, multiple ECG morphology templates corresponding to each of a number of different patient postures are acquired and stored for use in detecting a cardiac condition.

10 Claims, 6 Drawing Sheets

TEMPLATE MATCHING METHOD FOR MONITORING OF ECG MORPHOLOGY CHANGES

TECHNICAL FIELD

The disclosure relates generally to medical devices and, in particular, to monitoring changes in ECG morphology.

BACKGROUND

Numerous pathological conditions alter the morphology of the ECG signal. For example, cardiac ischemia or an infarct can be diagnosed by observing changes in the ST segment using skin electrodes for acquiring a 12-lead surface ECG. Changes in the R-wave morphology may be indicative of conduction disorders such as bundle branch block. In a clinic, ECG morphology changes can be detected under controlled conditions for diagnosing a change in the cardiac health of the patient.

Implantable and external cardiac monitoring devices can provide ambulatory monitoring of a patient's ECG signal using subcutaneous electrodes or skin electrodes. This ECG data can be used to detect cardiac events that may not occur during an office visit. Data may be transmitted to a programmer or via a remote patient monitoring network to a clinic for review by a clinician. Such ambulatory monitoring of the ECG is useful for detecting arrhythmias based on changes in heart rate. The R-wave of a subcutaneous ECG signal is relatively high amplitude and can be sensed reliably for determining a heart rate.

Detection of morphology changes of a subcutaneous ECG signal is more challenging than R-wave sensing. Bipolar electrodes incorporated on the housing a subcutaneous device are spaced much closer together than 12-lead surface ECG electrodes. This spacing makes the subcutaneous ECG signal morphology prone to changes caused by postural changes of the patient. Even surface ECG monitoring using an ambulatory device may be prone to postural effects since the skin electrodes may be placed closer together with fewer leads recorded than during a 12-lead ECG evaluation. A 12-lead surface ECG is generally acquired when the patient is in a controlled posture the various leads will not all be affected by posture in the same manner allowing accurate diagnoses to still be made. Implantable devices that utilize intracardiac electrodes, such as pacemakers, are less prone to the affects of posture changes since the electrodes are positioned in and sense directly in the heart. The resulting EGM signals are higher in amplitude than the subcutaneous ECG signals. It is desirable, however, to provide ambulatory monitoring of the subcutaneous ECG (or surface ECG) for detecting ECG signal morphology changes associated with various cardiac conditions.

DETAILED DESCRIPTION

Figure 1:
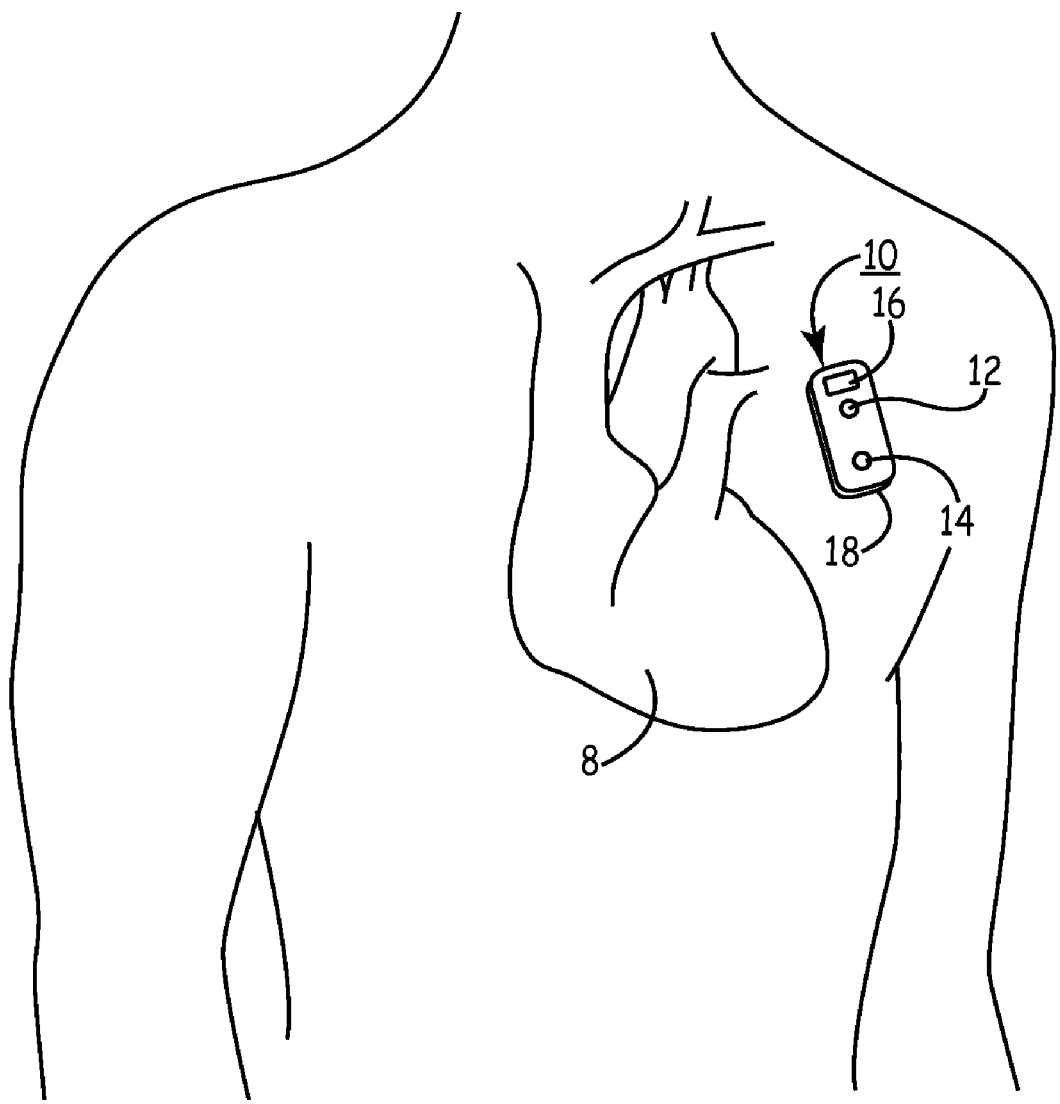
FIG. 1 is an illustration of an implantable medical device (IMD) implanted in a patient for monitoring the patient's heart.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is an illustration of an implantable medical device (IMD) 10 implanted in a patient for monitoring the patient's heart 8. IMD 10 is embodied as an implantable monitoring device for recording the patient's ECG, which is sensed subcutaneously using a bipolar pair of electrodes 12 and 14. The subcutaneous ECG signal can be sensed continuously with data written temporarily to memory in a looping manner until long-term data storage is triggered. Long-term data storage may be triggered automatically upon detecting a cardiac event or manually by the patient using an external device (not shown).

IMD 10 includes a posture sensor 16 embodied as an accelerometer. Sensor 16 may be a one-, two- or three-dimensional accelerometer. In one embodiment sensor 16 is embodied as a three-dimensional accelerometer used for determining a patient's posture, for example as generally disclosed in U.S. Pat. No. 5,593,431, (Sheldon, et al.), hereby incorporated herein by reference in its entirety. Sensor 16 is shown mounted within a hermetically-sealed housing 18 that encloses IMD circuitry and other components (not shown).

It is recognized that in various embodiments, IMD 10 may alternatively include one or more leads, extending from a connector block hermetically joined to housing 18, and carrying one or more electrodes and/or sensor 16. Such leads may be tunneled to subcutaneous locations. Furthermore, while IMD 10 is shown as a subcutaneous, "leadless" device used only for cardiac monitoring, practice of the present invention is not limited to such a device. Other devices in which embodiments of the present invention may be implemented include both therapy delivery and monitoring devices as well as devices that utilize leads extending therefrom for carrying electrodes and/or sensors. Such devices may include implantable pacemakers, defibrillators, drug delivery pumps, neurostimulators or the like as well as external devices that perform ambulatory ECG monitoring. Leads associated with such devices may include subcutaneous leads, transthoracic leads, transvenous leads, intracardiac leads, surface leads and so on.

Figure 2:
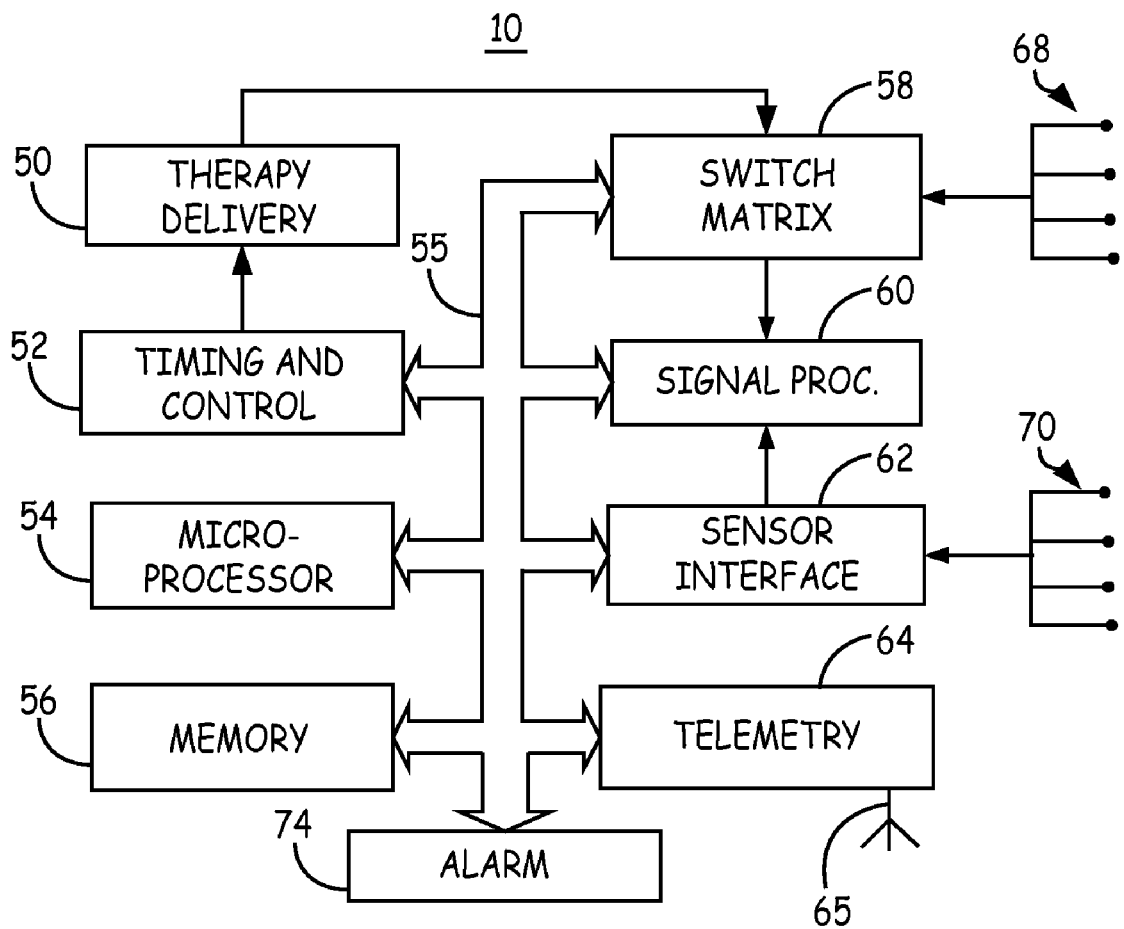
FIG. 2 is a functional block diagram of an IMD in which embodiments of the present invention may be implemented.

FIG. 2 is a functional block diagram of an IMD 20 in which embodiments of the present invention may be implemented. IMD 20 generally includes timing and control circuitry 52 and an operating system that may employ microprocessor 54 or a digital state machine for timing sensing and therapy delivery functions (when present) in accordance with a programmed operating mode. Microprocessor 54 and associated memory 56 are coupled to the various components of IMD 20 via a data/address bus 55. IMD 20 may include a therapy delivery module 50 for delivering a therapy in response to determining a need for therapy based on sensed physiological signals. Therapy delivery module 50 may provide drug delivery therapies or electrical stimulation therapies, such as cardiac pacing or anti-arrhythmia therapies. Therapies are delivered by module 50 under the control of timing and control 52. Therapy delivery module 50 is typically coupled to two or more electrode terminals 68 via an optional switch matrix 58. Switch matrix 58 may be used for selecting which electrodes and corresponding polarities are used for delivering electrical stimulation pulses. Terminals 68 may be coupled to connectors providing electrical connection to electrodes incorporated in IMD housing (as shown in FIG. 1) or other lead-based electrodes when available.

Electrode terminals 68 are also used for receiving cardiac electrical signals. Cardiac electrical signals may be monitored for use in diagnosing or monitoring a patient condition or may be used for determining when a therapy is needed and in controlling the timing and delivery of the therapy. When used for sensing, electrode terminals 68 are coupled to signal processing circuitry 60 via switch matrix 58. Signal processor 60 includes sense amplifiers and may include other signal conditioning circuitry and an analog-to-digital converter. Electrical signals may then be used by microprocessor 54 for detecting a cardiac condition, such as a change in cardiac conduction, ischemia, an infarct or other cardiac conditions. As used herein, a "cardiac condition" is a pathological condition that can be present during normal sinus rhythm, as opposed to a cardiac arrhythmia which can also be detected from ECG signals but is a pathological heart rhythm, i.e. non-sinus rhythm, characterized by a heart rate that is too slow (bradycardia) or too fast (tachycardia or fibrillation). As such, a cardiac condition detected using an ECG signal as described herein, in particular a subcutaneous ECG signal using subcutaneous electrodes such as the electrode pair 12 and 14 shown in FIG. 1, is not a condition related to detecting a change in heart rate per se but is related to detecting a change in ECG morphology during normal sinus rhythm that occurs as a result of a cardiac condition. The heart rhythm may undergo a rate change as a secondary effect of a cardiac condition, for example a conduction disorder, but remains in normal sinus rhythm.

IMD 10 may additionally be coupled to one or more physiological sensors via physiological sensor terminals 70. Physiological sensors may include pressure sensors, accelerometers, flow sensors, blood chemistry sensors, activity sensors or other physiological sensors known for use with implantable devices. Physiological sensors may be carried by leads extending from IMD 20 or incorporated in or on the IMD housing. In particular, at least one sensor responsive to posture changes of the patient is coupled to sensor terminals 70. The posture sensor is used to monitor patient posture in conjunction with ECG monitoring for detecting cardiac conditions. An ECG morphology change may be caused by a change in patient posture and not at all associated with a cardiac condition. On the other hand, an ECG morphology change can be caused by a cardiac condition and unrelated to a change in patient posture, or a combination of both a cardiac condition and a change in patient posture. As such, methods described herein allow for the detection of a cardiac condition independent of the presence of patient posture-induced ECG changes.

Signals received at sensor terminals 70 are received by a sensor interface 62 which provides sensor signals to signal processing circuitry 60. Sensor signals are used by microprocessor 54 for detecting physiological events or conditions. In particular, signals from sensor 16 are received for determining a patient posture or a change in patient posture. Posture data is provided to microprocessor 54 and may be stored for use in diagnosing or monitoring the patient.

The operating system includes associated memory 56 for storing a variety of programmed-in operating mode and parameter values that are used by microprocessor 54. The memory 56 may also be used for storing data compiled from sensed physiological signals and/or relating to device operating history for telemetry out on receipt of a retrieval or interrogation instruction. Microprocessor 54 may respond to ECG and posture data by altering a therapy, triggering data storage, enabling other sensors for acquiring physiological data, or triggering alert 74 to generate an alert signal to the patient or a caregiver that a serious condition has been detected that may require medical intervention. Data relating to a detected ECG morphology change may be stored in memory 56 for later retrieval using an external programmer or for uplinking to a patient's home monitor or remote patient management database.

IMD 10 further includes telemetry circuitry 64 and antenna 65. Programming commands or data are transmitted during uplink or downlink telemetry between IMD telemetry circuitry 64 and external telemetry circuitry included in a programmer or monitoring unit (not shown). Telemetry circuitry 64 and antenna 65 may correspond to telemetry systems known in the art.

Figure 3:
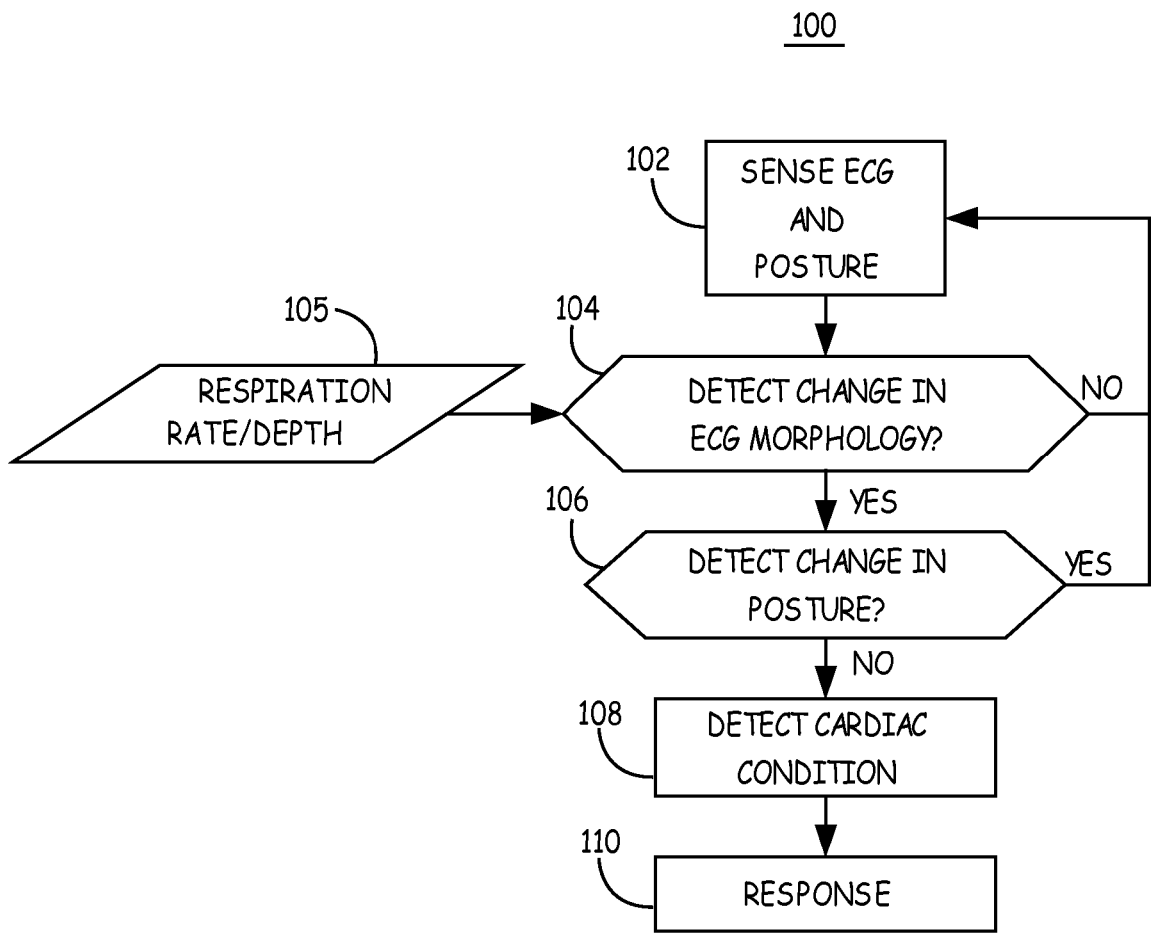
FIG. 3 is a flow chart of a method for monitoring a patient according to one embodiment.

FIG. 3 is a flow chart of a method for monitoring a patient according to one embodiment of the invention. Flow chart 100 is intended to illustrate the functional operation of the device, and should not be construed as reflective of a specific form of software or hardware necessary to practice the invention. It is believed that the particular form of software will be determined primarily by the particular system architecture employed in the device and by the particular sensing and therapy delivery methodologies employed by the device. Providing software to accomplish the present invention in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 102, an ECG signal and a posture signal are sensed. The IMD monitors for a change in ECG morphology at decision block 104. A change in morphology may be detected using numerous algorithms. In one embodiment, a sensing window is set relative to a sensed ECG event, such as a P-wave, R-wave or T-wave. The sensing window may include all of the P-wave, QRS complex, and T-wave or any desired portions of the ECG signal. The portions of the ECG signal that are specifically monitored may depend on particular patient needs and relate to the cardiac condition(s) being monitored for. The ECG signal within the sensing window may then be digitized and compared to a reference signal template to determine if a change has occurred. In one embodiment, the reference signal template may be a running average of multiple ECG signals. In other embodiments, as will be further described below, the reference signal template may be previously acquired and associated with a particular patient position.

In one embodiment, an ECG signal may be compared on a beat-by-beat basis to a running average of several ECG signals or to a predetermined template to detect a morphology change. If a predetermined number of ECG signals differ from the running average by more than a predetermined amount, a change is detected. The detection of a change in ECG morphology may involve comparisons of peak amplitudes, zero-crossing, signal widths, signal slopes or any other features of the ECG signal. Comparisons may further involve various waveform analysis methods such as Correlation Waveform Analysis (CWA), Area of Difference Analysis (AD), wavelet transform analysis, or other methods. Examples of ECG template acquisition and ECG signal analysis methods are generally disclosed in U.S. Pat. No. 6,393,316 (Gillberg, et al.) and U.S. Pat. No. 7,062,315 (Koyrakh, et al.), both of which patents are incorporated herein by reference in their entirety.

Detection of a change in ECG signal morphology may include evaluating the respiration component of the ECG signal as indicated at block 105. The respiration effects on the ECG can be evaluated by examining low frequency changes (e.g. 0.5 Hz) of R-wave amplitude or heart rate for example. Respiration may also be detected using methods known in the art for monitoring a thoracic impedance signal. Since a deep breathing, breath holding, or change in respiration rate can all affect the ECG, the analysis performed at block 104 may include checking for a respiration change or a respiratory effect on the ECG.

If no change in ECG signal morphology is detected, the IMD continues to monitor the ECG signal. When a morphology change is detected at block 104, the IMD determines if a posture change has also been detected at block 106. Accordingly, the IMD may be acquiring the posture signal and storing it in temporary memory such that it is available upon detecting an ECG morphology change. The detected morphology change triggers an analysis of the posture signal before and just after the detected morphology change to determine if a posture change has occurred coincidentally with the ECG morphology change. In other words, if one posture is detected just prior to the ECG morphology change, and a different posture is detected, for example within 30 seconds of the ECG morphology change, the posture change is considered to be coincident with the ECG morphology change.

If no posture change is detected, a cardiac condition corresponding to the detected morphology change is detected at block 108. A detected morphology change may relate to a number of cardiac conditions, including but not limited to, a conduction disorder, ischemia or infarct, electrolyte imbalance, pro-arrhythmic effect of drugs, cardiac hypertrophy, and cardiac dilation. A specific cardiac condition may be detected by the IMD based on analysis of the ECG morphology change or a morphology change may be detected as a general indication that a cardiac condition warranting further clinical investigation or medical treatment may be present. At block 110 the IMD responds appropriately. Appropriate responses may depend on the morphology change detected and may include triggering long-term storage of the ECG data and the posture data, generating a patient alarm, initiating a data transfer to an external device, or initiating a therapy when therapy delivery is available.

If a posture change is detected at block 106, the change in the ECG morphology may be assumed to be caused by the posture change. As such, in one embodiment, detection of a posture change at block 106 precludes the detection of a cardiac condition in response to the detected ECG morphology change. The IMD continues to monitor the ECG morphology by returning to block 102. Since an ECG morphology change can result from both a posture change and a cardiac condition, however, further analysis of the morphology change is generally desirable in the presence of a posture change.

Figure 4:
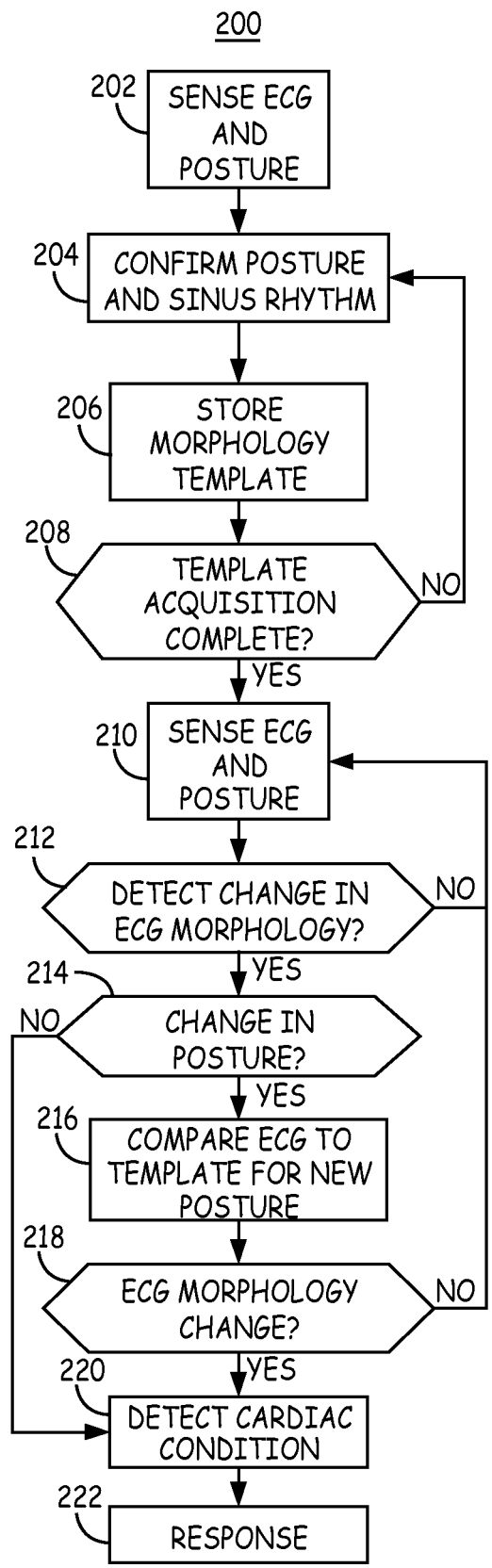
FIG. 4 is a flow chart of a method for detecting a cardiac condition based on ECG morphology and posture.

FIG. 4 is a flow chart of a method for detecting a cardiac condition based on ECG morphology and posture. Initially, ECG morphology templates representing a baseline ECG morphology recorded during different but stable patient postures are acquired and stored. At block 202 the ECG signal and posture signal are sensed. At block 204, the patient's posture is confirmed and verified to be stable. A stable posture may be confirmed based on the posture sensor signal alone or may be based on manual input, or a combination of both. For example, the posture sensor signal may be used to verify a stable upright standing position, upright sitting position, left-side lying, right-side lying, supine or prone position. Alternatively, the patient may be instructed to assume a position and the patient's current posture may communicated to the IMD through telemetry using a programmer or other external device. The implanted posture sensor may then verify that the programmed posture remains stable prior to and during template acquisition. A stable patient posture is a posture that is unchanging or remaining within a predefined range, for a predetermined amount of time, for example 10 seconds to 60 seconds, which may include an interval of time prior to acquiring an ECG signal and through ECG signal acquisition for generating a template.

Once a posture is verified and stable, an ECG morphology template is generated and stored at block 206. An ECG morphology template may be generated by digitizing and averaging a predetermined number of consecutively or non-consecutively sensed cardiac cycles, e.g. 3 to 8 cardiac cycles. It is recognized that the stability of the ECG signal can be verified prior to generating the template. For example, template generation may be postponed when the ECG signal is determined to by noisy or the heart rate is not determined to be normal sinus rhythm, i.e. an arrhythmia is being detected.

The ECG morphology template is stored for the given posture. At block 208, the IMD determines if the template acquisition is complete for all desired patient postures. If not, method 200 returns to block 204 to detect and confirm a different patient posture and repeat the ECG morphology template generation and storage for that posture.

The number and type of postures for which ECG templates are stored may vary between embodiments and between patients. The effect of posture on the ECG signal may vary in different embodiments and will depend on the positioning and orientation of the sensing electrodes and other factors. It is expected that ECG morphology templates are generated and for at least two patient postures, e.g. corresponding to a generally upright position and a lying position. Depending on the effect of posture on the ECG signal and the sensitivity desired for detecting morphology changes, templates corresponding to additional postures such as sitting versus standing and right-side lying, left-side lying, supine and prone positions may be generated and stored.

Once template acquisition is complete, the ECG signal and the posture signal are sensed at block 210 for ongoing, ambulatory monitoring of the patient. Sensing of ECG and posture signals may be continuous or intermittent depending on the desired frequency for monitoring for a cardiac condition. In some situations, continuous monitoring is desired to detect sudden and serious cardiac conditions, such as an infarct. In other situations, intermittent monitoring, such as hourly or daily monitoring, may be adequate for detecting more gradual changes or changes that do not require immediate medical attention. The sensed signals may be stored temporarily, e.g. in a looping manner, such that data is stored for an interval of time until it is overwritten by new data or until a cardiac condition or other trigger event is detected causing data to be permanently stored for later retrieval by a clinician. As used herein, "permanent" data storage refers to data that is stored until retrieved by an external device or cleared by a user.

As the ECG signal is sensed, it is compared to a reference template to determine if the ECG morphology is changed. As described above, the ECG signal morphology may be compared to a running average of the ECG or it may be compared to one of the previously stored morphology templates corresponding to a patient posture. Comparison to a previously stored template requires knowing the patient's current posture. As such, the posture signal sensed at block 210 is used to determine the posture, and the determined posture is used, in turn, to select which stored ECG template the current ECG signal will be compared to.

The ECG morphology can change during an arrhythmia. As such, if a rate change is detected, a cardiac condition may or may not be detected. Method 200 of FIG. 4 and other methods described herein preferably operate during normal sinus rhythm such that morphological changes of the ECG representative of pathological cardiac conditions can be detected and diagnosed. As such, methods employed at block 212 for detecting a change in morphology may explicitly include verifying normal sinus rhythm, which may be based on cardiac cycle intervals and cardiac cycle event patterns. Reference is made, for example, to U.S. Pat. No. _____, hereby incorporated herein by reference in its entirety.

If a change in the ECG signal morphology is detected at block 212, a determination is made at block 214 whether the patient's posture has changed coincidentally with the morphology change. A change in posture may be detected by detecting an unstable posture signal or by comparing the posture just prior to the detected ECG change or just after the detected ECG change to a posture at an earlier time prior to the detected ECG change. As such, a posture change defined to be coincident with an ECG morphology change may be detected just before or just after the ECG morphology change and occurs, in less than about 10 seconds, for example within about 2 seconds, of the detected morphology change in one embodiment. A posture change coincident with a detected morphology change, however, may be defined to be a change that occurs within up to about one minute of the detected ECG morphology change. The definition of a coincident posture change will in part depend on the algorithm and number of heart beats used to detect the ECG morphology change. If the posture has not changed coincidentally with the morphology change, the ECG morphology change is likely due to a change in a cardiac condition as detected at block 220. The ECG morphology may also change in a time-dependent manner, for example during a transient ischemic episode. The ST segment may vary for several seconds or minutes and finally return to a steady state as the ischemic episode resolves. As such, if a time-varying morphology is detected that persists after the first few seconds following a posture change, a cardiac condition is indicated.

The cardiac condition detected at block 220 may vary between embodiments and may require additional ECG signal analysis. In one embodiment, cardiac ischemia or an infarct may be detected based on changes in the T-wave or the ST segment. Bundle branch block or other conduction disorders may be may be detected in response to changes in the R-wave morphology. In some embodiments, a specific condition may not be detected. Instead, the detected change in morphology triggers a response such as data storage or a data transfer at block 222 such that the ECG data may be examined by a clinician or analyzed by an external computer for making an appropriate diagnosis. If a serious cardiac condition is detected, a patient alarm may be generated to alert the patient that medical attention may be warranted.

If a change in posture is detected at block 214, an ECG morphology template corresponding to the new posture is selected at block 216. The current ECG signal is then compared to the template corresponding to the current patient posture. If the current ECG signal matches the template corresponding to the current posture, as determined at decision block 218, the ECG morphology change detected at block 212 is concluded to be the result of the coincident posture change. The IMD continues to monitor the ECG morphology and the posture by returning to block 210. Template matching criteria can be defined differently in different embodiments of the invention. A template match may be defined as an ECG signal characteristic or feature that is within a predefined percentage, standard deviation, or otherwise defined acceptable range of the corresponding template characteristic or feature. Template matching criteria may include time-dependent criteria defined according to the time since template generation. In other words, a greater difference between the template and the current ECG signal may be acceptable as the template becomes older.

If the current ECG morphology does not match the template corresponding to the current patient posture, as determined at block 218, the morphology change detected at block 212 may be caused by both the posture change and a change in a cardiac condition. A cardiac condition is detected at block 220 in response to the difference between the current ECG signal morphology and the morphology template for the current patient posture. The detection at block 220 may be based on the detected morphology difference or may require additional ECG signal processing. A response to the detected condition is provided at block 222.

Figure 5:
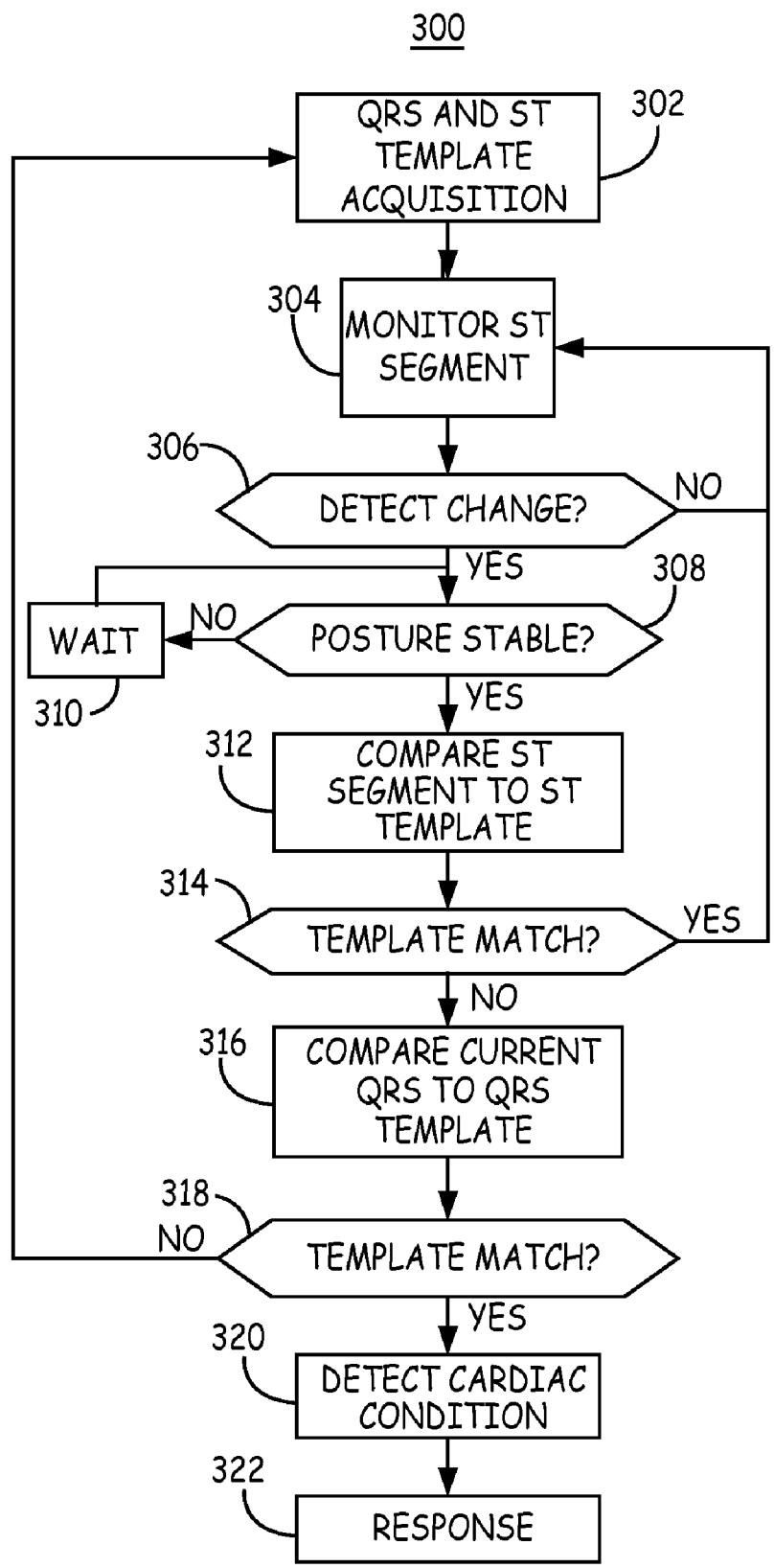
FIG. 5 is a flow chart of a method for detecting a cardiac condition based on ECG and posture signals according to another embodiment of the present invention.

FIG. 5 is a flow chart of a method for detecting a cardiac condition based on ECG and posture signals according to another embodiment of the present invention. At block 302, the ECG morphology templates for multiple patient positions are acquired and stored as generally described in conjunction with FIG. 4. In method 300, however, separate templates may be stored for different time segments or portions of the cardiac cycle. For example, a QRS signal template and a separate ST segment template may be generated for each patient posture using the sensed segments from one or more cardiac cycles. During patient monitoring beginning at block 304, the ECG signal is sensed and only one segment of the cardiac cycle may be monitored for morphology changes, for example the ST segment as shown in FIG. 5. Certain cardiac conditions can be diagnosed based on changes of a particular feature of the ECG signal. In some situations, the effects of posture on the ECG signal may be more readily detected in some segments of the ECG signal than others. As such, it may be desirable to monitor for signal changes in a particular segment of the ECG.

If a change in the selected ECG signal segment is detected as determined at decision block 306, the posture signal may be examined at block 308. If the posture signal is unstable, method 300 advances to block 310 to wait for an interval of time. An unstable posture signal is a signal that is changing by more than a predefined range within a given interval of time, for example within 30 seconds. Method 300 may wait a predetermined interval of time, for example 10 to 30 seconds, then recheck the posture at block 308. Alternatively, method 300 may wait a variable interval of time at block 310 while continuously monitoring the posture signal until a stable posture is verified.

Once a stable posture is verified, the current ST segment morphology is compared to an ST segment template at block 314 corresponding to the currently detected posture. If the current ST segment morphology matches the template, method 300 returns to block 304 to continue monitoring the ST segment. No cardiac condition is detected.

If the current ST segment morphology does not match the stored template corresponding to the current patient posture, as determined at block 314, the method 300 may additionally compare other segments of the ECG signal to the appropriate template. For example, a QRS template corresponding to the current patient posture may be compared to the current QRS signal. If the QRS signal has also changed, particularly by a similar magnitude difference, the stored template may no longer be valid and method 300 may return to block 302 to update the template(s) for one or more patient postures. However, if the QRS morphology matches the stored template at block 318, a cardiac condition is detected at block 320 based on the change in the ST segment. An appropriate response is provided at block 322.

Figure 6:
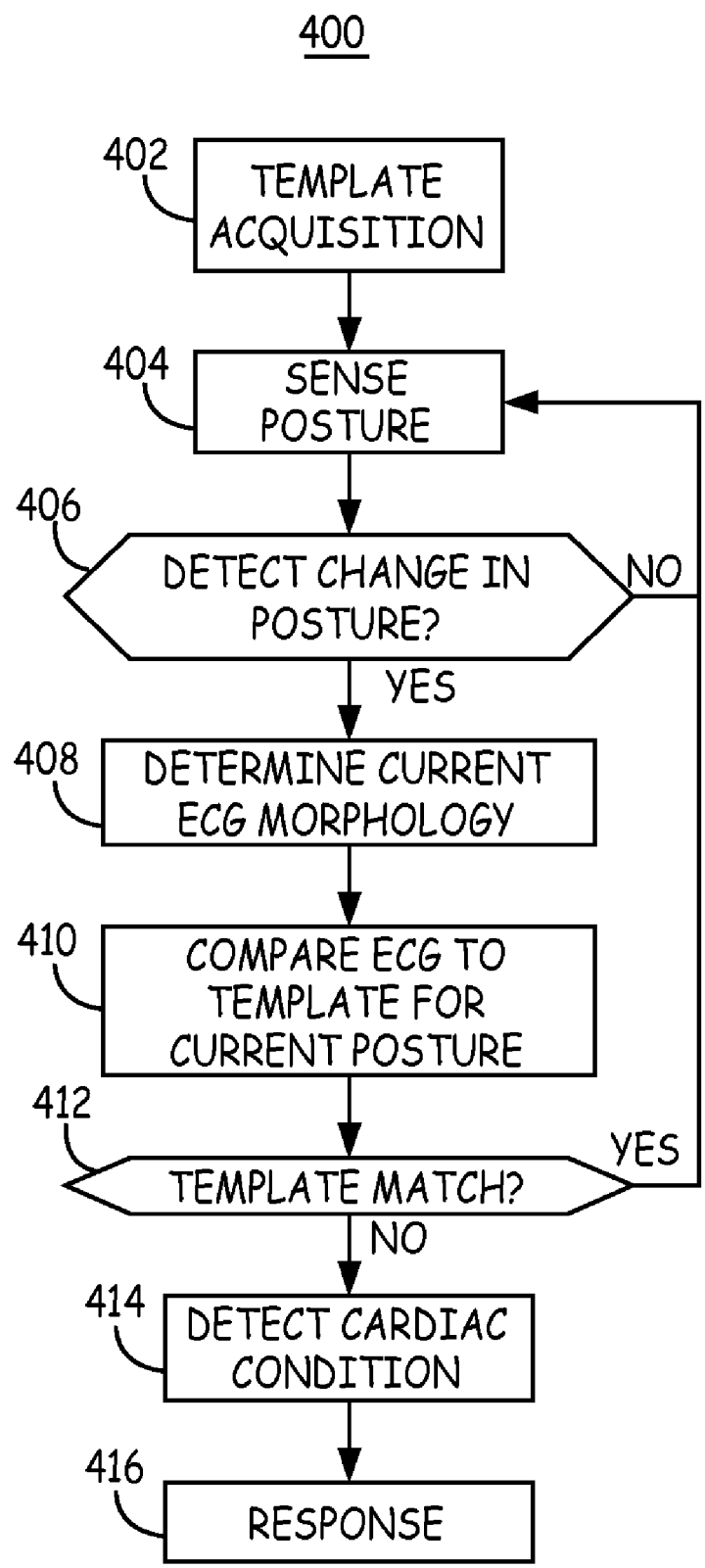
FIG. 6 is a flow chart of a method for checking a patient's ECG signal morphology in response to a posture change.

FIG. 6 is a flow chart of a method 400 for checking a patient's ECG signal morphology in response to a posture change. In some embodiments of the invention, where less frequent ECG monitoring is required, the ECG morphology may be examined in response to a detected posture change. At block 402, the ECG morphology templates corresponding to at least two different patient postures are acquired and stored as described previously. At block 404, a posture signal is sensed for detecting a change in patient posture, as indicated by decision block 406. When a change in posture is detected, the current ECG morphology is determined at block 408 and compared to the ECG template corresponding to the currently detected posture at block 410.

If the current ECG morphology matches the template, method 400 continues to monitor posture without detecting a cardiac condition. If the current ECG morphology does not match, a cardiac condition is detected at block 414 based on the changed ECG morphology and/or additional signal analysis. An appropriate response is provided at block 416. Thus for each posture change, the ECG morphology is rechecked. This may result in a variable number of monitoring sessions per day. In some embodiments a maximum number of ECG morphology checks per day, per hour, or per minute, etc. may be defined to prevent excessively frequent ECG morphology checks. A maximum number of ECG morphology checks per day (or per hour, per minute etc.) may be defined for each patient posture as well such that if the ECG morphology has been examined a certain number of times for a given posture, detection of the same posture will not trigger the ECG morphology comparison at block 410.

Thus, have been presented in the foregoing description with reference to specific embodiments. It is appreciated that various modifications to the referenced embodiments may be made without departing from the scope of the invention as set forth in the following claims.

The invention claimed is:

1. A method for use in an implantable medical device, comprising:
   sensing a subcutaneous ECG signal in a patient;
   sensing a signal corresponding to a posture of the patient;
   detecting a cardiac condition in response to the ECG signal and the posture signal;
   detecting a change in a morphology of the ECG signal in response to the ECG signal; and
   detecting an unstable posture of the patient in response to the posture signal; and
   wherein detecting a cardiac condition comprises waiting for a stable posture signal to be detected.

2. The method of claim 1, wherein detecting a cardiac condition comprises determining if the patient posture has changed.

3. The method of claim 1, further comprising:
   detecting a plurality of patient postures in response to the posture signal;
   acquiring and storing an ECG morphology template corresponding to each of the plurality of patient postures;
   wherein detecting a cardiac condition comprises
      determining a current ECG signal morphology,
      determining a current patient posture,
      selecting one of the stored ECG morphology templates corresponding to the current patient posture; and
      comparing the current ECG signal morphology to the selected one of the ECG morphology templates.

4. The method of claim 3, further comprising
   detecting a change in patient posture,
   wherein the current ECG signal morphology is determined in response to detecting the change in patient posture.

5. A method for use in an implantable medical device, comprising:
   sensing a subcutaneous ECG signal in a patient;
   sensing a signal corresponding to a posture of the patient;
   detecting a cardiac condition in response to the ECG signal and the posture signal;
   detecting a plurality of patient postures in response to the posture signal; and
   acquiring and storing an ECG morphology template corresponding to each of the plurality of patient postures;
   wherein detecting a cardiac condition comprises
      determining a current ECG signal morphology,
      determining a current patient posture,
      selecting one of the stored ECG morphology templates corresponding to the current patient posture; and
      comparing the current ECG signal morphology to the selected one of the ECG morphology templates;
   wherein acquiring and storing the ECG morphology template corresponding to each of the plurality of patient postures comprises storing a first template corresponding to a first ECG signal portion and a second template corresponding to a second ECG signal portion, the first and second signal portions each occurring at different times within a cardiac cycle,
   wherein detecting a cardiac condition comprises determining if the current ECG signal morphology matches a single one of the first and second templates corresponding to the current patient posture.

6. A medical device, comprising:
   a pair of subcutaneous ECG electrodes for sensing an ECG signal in a patient;
   a sensor for sensing a signal corresponding to a posture of the patient;
   a processor coupled to the ECG electrodes and the posture sensor and configured to detect a cardiac condition in response to the ECG signal and the posture signal, wherein detecting a cardiac condition comprises:
   detecting a change in a morphology of the ECG signal in response to the ECG signal;
   detecting an unstable posture of the patient in response to the posture signal; and
   waiting for a stable posture signal to be detected.

7. The device of claim 6 wherein detecting a cardiac condition comprises determining if the patient posture has changed.

8. The device of claim 6 further comprising a memory coupled to the processor,
   wherein the processor is further configured to detect a plurality of patient postures in response to the posture signal, and acquire and store in the memory an ECG morphology template corresponding to each of the plurality of patient postures;
   wherein detecting a cardiac condition comprises determining a current ECG signal morphology, determining a current patient posture,
      selecting one of the stored ECG morphology templates corresponding to the current patient posture; and
      comparing the current ECG signal morphology to the selected one of the ECG morphology templates.

9. The device of claim 8 wherein the processor is further configured to detect a change in patient posture,
   wherein the current ECG signal morphology is determined in response to detecting the change in patient posture.

10. A medical device, comprising:
   a pair of subcutaneous ECG electrodes for sensing an ECG signal in a patient;
   a sensor for sensing a signal corresponding to a posture of the patient;
   a processor coupled to the ECG electrodes and the posture sensor and configured to detect a cardiac condition in response to the ECG signal and the posture signal;
   wherein the processor is further configured to detect a plurality of patient postures in response to the posture signal, and to acquire and store in the memory an ECG morphology template corresponding to each of the plurality of patient postures;
   wherein detecting a cardiac condition comprises determining a current ECG signal morphology, determining a current patient posture,
      selecting one of the stored ECG morphology templates corresponding to the current patient posture; and
      comparing the current ECG signal morphology to the selected one of the ECG morphology templates;
   wherein detecting a cardiac condition comprises determining if the current ECG signal morphology matches a single one of the first and second templates corresponding to the current patient posture.

* * * * *